(12) United States Patent
Jagadish et al.

(10) Patent No.: US 10,717,700 B2
(45) Date of Patent: Jul. 21, 2020

(54) NITRATION OF AROMATIC COMPOUNDS

(71) Applicants: Arizona Board of Regents for the University of Arizona, Tucson, AZ (US); Bhumasamudram Jagadish, Tucson, AZ (US); Eugene Mash, Tucson, AZ (US)

(72) Inventors: Bhumasamudram Jagadish, Tucson, AZ (US); Eugene Mash, Tucson, AZ (US)

(73) Assignee: Arizona Board of Regents on behalf of the University of Arizona, Tucson, AZ (US)

(*) Notice: Subject to any disclaimer, the term of this patent is extended or adjusted under 35 U.S.C. 154(b) by 19 days.

(21) Appl. No.: 15/550,233

(22) PCT Filed: Jan. 18, 2016

(86) PCT No.: PCT/US2016/013795
§ 371 (c)(1),
(2) Date: Aug. 10, 2017

(87) PCT Pub. No.: WO2016/118450
PCT Pub. Date: Jul. 28, 2016

(65) Prior Publication Data
US 2018/0179144 A1    Jun. 28, 2018

Related U.S. Application Data

(63) Continuation of application No. 62/105,269, filed on Jan. 20, 2015.

(51) Int. Cl.
*C07C 201/08*    (2006.01)

(52) U.S. Cl.
CPC ........ *C07C 201/08* (2013.01); *C07B 2200/05* (2013.01)

(58) Field of Classification Search
CPC .................................................. C07C 201/08
See application file for complete search history.

(56) References Cited

U.S. PATENT DOCUMENTS

| | | | | | |
|---|---|---|---|---|---|
| 2,007,234 | A | * | 7/1935 | Wirth | C07C 205/37 568/584 |
| 3,221,062 | A | * | 11/1965 | Wright | C07C 201/08 568/706 |
| 4,746,642 | A | * | 5/1988 | Schumacher | B01J 27/24 502/200 |
| 5,663,441 | A | * | 9/1997 | Kwiatkowski | C07C 209/18 564/399 |
| 2010/0298567 | A1 | * | 11/2010 | Roberge | B01J 19/0093 544/322 |
| 2011/0178199 | A1 | * | 7/2011 | Enomura | B01F 3/0807 522/3 |

FOREIGN PATENT DOCUMENTS

| | | | | |
|---|---|---|---|---|
| WO | WO9636587 | * | 11/1996 | ........... C07C 201/08 |
| WO | WO2012049513 A1 | * | 4/2012 | ........... C07C 201/08 |

OTHER PUBLICATIONS

ThermoFischer Scientific (Safety data sheet for fuming Nitric acid, created Feb. 5, 2010, pp. 1-8). (Year: 2010).*
Jagadish et al. ("Synthesis of 13C and 15N labeled 2,4-dinitroanisole", Journal of Labelled Compounds and Radiopharmaceuticals, vol. 57, Issue 6, 2014, pp. 434-436).*
Hoggett et al. ("The Duality of Mechanism for Nitration in Acetic Anhydride", Chemical Communications, 1969, pp. 605-606).*
Bourne et al. ("Studies of Trifluoroacetic Acid. Part V. Trifluoroacetic Anhydride as a Condensing Agent in Reaction of Nitrous and Nitric Acids", J. Chem. Soc., 1952, pp. 1695-1696).*
Smith et al. ("A novel method for the nitration of deactivated aromatic compounds", J. Chem. Soc. Perkin Trans. 1, 2000, pp. 2753-2758).*
Kulkarni ("Continuous flow nitration in miniaturized devices", Beilstein Journal of Organic Chemistry, 2014, pp. 405-424.*

* cited by examiner

*Primary Examiner* — Rosalynd A Keys
(74) *Attorney, Agent, or Firm* — Don D. Cha; HDC IP Law, LLP

(57) ABSTRACT

The present invention provides a process for nitrating aromatic compounds without the need for a solid catalyst and/or any organic solvents and/or any other additives. A typical process includes combining or admixing a nitric acid and an anhydride compound under conditions sufficient to produce a reactive intermediate. The aromatic compound to be nitrated is then added to this reactive intermediate to produce a nitroaromatic compound. The nitroaromatic compound can be substituted with one or more, typically, one to three, and often one or two nitrate ($—NO_2$) groups.

6 Claims, No Drawings

NITRATION OF AROMATIC COMPOUNDS

CROSS-REFERENCE TO RELATED APPLICATIONS

This application claims the priority benefit of U.S. Provisional Application No. 62/105,269, filed Jan. 20, 2015, which is incorporated herein by reference in its entirety.

STATEMENT REGARDING FEDERALLY FUNDED RESEARCH

This invention was made with government support under grant number ER-2221 awarded by the Strategic Environmental Research and Development Program. The government has certain rights in the invention.

FIELD OF THE INVENTION

The present invention relates to a process for nitrating aromatic compounds without the need for a solid catalyst and/or any organic solvents.

BACKGROUND OF THE INVENTION

Nitrations of aromatic compounds, such as benzene and substituted benzene derivatives, are well known in the art. Typically, a conventional nitration reaction requires a solid catalyst, such as claycop (see Gigante et al., *JOC*, 1995, 60, 3445-3447), or relatively expensive reagent(s) such as the ionic liquid ethylammonium nitrate (EAN) (see Gopalakrishnan et al., *JOC*, 2011, 76, 8088-8094), or require relatively harsh conditions, e.g., sulfuric acid solvent. Unfortunately, most, if not all, conventional methods require rather expensive and/or labor intensive processes to obtain a relatively pure nitroaromatic compound.

Therefore, there is a continuing need for cost effective, simple and facile processes for nitrating aromatic compounds.

SUMMARY OF THE INVENTION

One particular aspect of the invention provides a process for nitrating an aromatic compound comprising:
  reacting a concentrated nitric acid with an anhydride in the absence of any inert organic solvent under conditions sufficient to produce a reaction mixture comprising an acylated nitrate intermediate compound;
  adding an aromatic compound to the reaction mixture under conditions sufficient to produce a nitrated aromatic compound; and
  separating the nitrated aromatic compound from the reaction mixture.

In some embodiments, said step of adding the aromatic compound to the reaction mixture comprises adding a solution of the aromatic compound in the anhydride.

In other embodiments, said aromatic compound comprises an electron donating group.

Yet in other embodiments, said aromatic compound is an optionally substituted phenyl compound. Within these embodiments, in some instances, said aromatic compound is anisole. In some such instances, the nitrated aromatic compound that is produced comprises 2,4-dinitroanisole. The yield of 2,4-dinitroanisole is at least 50%, typically at least 70%, and often at least 80%.

Another aspect of the invention provides a process for nitrating an optionally substituted phenyl compound comprising:
  (a) providing a reaction mixture consisting essentially of a mixture obtained by combining a concentrated nitric acid and an anhydride compound; and
  (b) adding an optionally substituted phenyl compound to said reaction mixture under conditions sufficient to produce a nitrated phenyl compound.

In some embodiments, said optionally substituted phenyl compound is anisole. The process is useful for producing 2,4-dinitroanisole.

Typically, the reaction temperature of said step (b) is about 30° C. or less. In some instances, the reaction temperature of said step (a) is about 10° C. or less.

Still in other embodiments, said anhydride compound is of the formula: $R^1-C(=O)-O-C(=O)-R^2$, where each of $R^1$ and $R^2$ is independently hydrogen, alkyl, haloalkyl, cycloalkyl, (cycloalkyl)alkyl, aryl or aralkyl. Typically, each of $R^1$ and $R^2$ is independently $C_1$-$C_6$ alkyl. Often each of $R^1$ and $R^2$ is independently methyl, ethyl, propyl, t-butyl, iso-butyl, iso-propyl, butyl, or halogenated alkyls such as trifluoromethyl. Other exemplary anhydrides include anhydrides having a ring structure such as succinic anhydride and the like, as well as aromatic anhydrides such as benzoic anhydride and the like.

Still another aspect of the invention provides a process for producing 2,4-dinitroanisole comprising: contacting a concentrated nitric acid with an alkyl anhydride to produce a reaction mixture consisting essentially of a mixture obtained by combining a concentrated nitric acid and an anhydride compound; and adding anisole to the reaction mixture to produce 2,4-dinitroanisole. Typically, the process further comprises the step of separating 2,4-dinitroanisole from the reaction mixture. Separated product can be further purified, for example, by recrystallization.

DETAILED DESCRIPTION OF THE INVENTION

Some aspects of the invention provide a process for nitrating an aromatic compound. In some embodiments, the process is achieved in the absence of any catalyst, organic solvents, and/or any additives. As used herein, the term "absence" means about 1% or less, typically about 0.5% or less, often about 0.1% or less of the material is present or used in the process. Yet in another embodiments, no detectable amount of catalyst, organic solvents and/or additives is used. It should be appreciated that some of the reagents may inadvertently contain some trace amount of solvent, however the process of the invention typically does not include adding any additional amount of solvents.

The processes of the invention are directed to producing nitroarenes from an aromatic compound. Exemplary aromatic compounds that can be nitrated using the process of the invention include, but are not limited to, benzene, furan, thiofuran and the like. Each of these aromatic compounds can be optionally substituted with an alkyl group, such as methyl, ethyl, isopropyl, and the like; hydroxy; alkoxy (such as methoxy, ethoxy, t-butoxy, propoxy, iso-propoxy, and the like), halide (such as fluoro, chloro, bromo and iodo); an amino group (including mono- or di-alkyl substituted, or acyl substituted (e.g., acetyl) amino groups); heteroalkyl (such as hydroxymethyl, cyanomethyl, $-[CH_2]_n CO_2 CH_3$ (where n is an integer from 0 to 12); alkoxyalkyl (i.e., -(alkylene)-O-alkyl); cyano; haloalkyl (i.e., alkyl group having one or more halides including perhaloalkyl); formyl; and the like. The aromatic compound can be substituted with one or more substituents. When substituted, the aromatic compound typically has one or more, often one or two, and most often one substituent. Typically when more than one substituent is present, each substituent is independently selected from those listed herein as well as other substituent groups that are known to one skilled in the art.

In some embodiments, the aromatic compound comprises one or more, typically one electron donating group. Electron donating groups are well known to one skilled in the art and include, but are not limited to, hydroxy, alkoxy, alkyl, amino (including mono- and dialkyl amino) group, and the like.

In one particular aspect, the process of the invention includes reacting a concentrated nitric acid (i.e., at least 98% purity, typically at least 99% purity, often at least 99.5% purity and most often at least 99.9% purity) with an anhydride in the absence of any inert organic solvent under conditions sufficient to produce a reaction mixture comprising an acylated nitrate intermediate compound. As used herein, the term "anhydride" refers to a moiety of the formula $R^1$—C(=O)—O—C(=O)—$R^2$, where $R^1$ and $R^2$ are independently alkyl, haloalkyl, aryl, cycloalkyl, aralkyl, (cycloalkyl)alkyl and the like. "Alkyl" refers to a saturated linear monovalent hydrocarbon moiety of one to twelve, typically one to six, carbon atoms or a saturated branched monovalent hydrocarbon moiety of three to twelve, typically three to six, carbon atoms. Exemplary alkyl groups include, but are not limited to, methyl, ethyl, n-propyl, 2-propyl, tert-butyl, pentyl, and the like. "Aryl" refers to a monovalent mono-, bi- or tricyclic aromatic hydrocarbon moiety of 6 to 15 ring atoms, which is optionally substituted with one or more, typically one, two, or three substituents within the ring structure. When two or more substituents are present in an aryl group, each substituent is independently selected. Exemplary aryl includes, but is not limited to, phenyl, 1-naphthyl, and 2-naphthyl, and the like, each of which can optionally be substituted. "Alkylene" refers to a saturated linear divalent hydrocarbon moiety of one to twelve, typically one to six, carbon atoms or a branched saturated divalent hydrocarbon moiety of three to twelve, typically three to six, carbon atoms. Exemplary alkylene groups include, but are not limited to, methylene, ethylene, propylene, butylene, pentylene, and the like. "Aralkyl" refers to a moiety of the formula —$R^bR^c$ where $R^b$ is an alkylene group and $R^c$ is an aryl group as defined herein. Exemplary aralkyl groups include, but are not limited to, benzyl, phenylethyl, 3-(3-chlorophenyl)-2-methylpentyl, and the like. "Cycloalkyl" refers to a non-aromatic, typically saturated or mono-unsaturated, monovalent mono-, bi- or tricyclic hydrocarbon moiety of three to fifteen ring carbons. The cycloalkyl can be optionally substituted with one or more, typically one, two, or three, substituents within the ring structure. When two or more substituents are present in a cycloalkyl group, each substituent is independently selected. Exemplary cycloalkyl includes, for example, cyclopropyl, cyclohexyl, 1,2-dihydroxycyclopropyl, and the like. The terms "cycloalkylalkyl" and "(cycloalkyl)alkyl" are used interchangeably herein and refer to a moiety of the formula —$R^dR^e$ where $R^d$ is an alkylene group and $R^e$ is a cycloalkyl group as defined herein. Exemplary cycloalkylalkyl groups include, but are not limited to, cyclopropylmethyl, cyclohexylpropyl, 3-cyclohexyl-2-methylpropyl, and the like. The term "heterocycloalkyl" refers to a non-aromatic mono-, bi- or tricyclic moiety of three to fifteen ring atoms in which one or more, typically one, two or three ring atoms are heteroatoms selected from N, O, or $S(O)_n$ (where n is an integer from 0 to 2), the remaining ring atoms being C, where one or two C atoms can optionally be a carbonyl group (i.e., —C(=O)—). The heterocycloalkyl ring can be optionally substituted with one or more, typically one, two, or three, substituents. When two or more substituents are present in a heterocyclyl group, each substituent is independently selected. Exemplary heterocyclyl groups include, but is not limited to, tetrahydropyranyl, piperidino, piperazino, morpholino and thiomorpholino, thiomorpholino-1-oxide, thiomorpholino-1,1-dioxide, and the like. "Heteroaryl" refers to a monovalent mono- or bicyclic aromatic moiety of 5 to 12 ring atoms containing one, two, or three ring heteroatoms selected from N, O, or S, the remaining ring atoms being C. The heteroaryl ring can be optionally substituted with one or more substituents, typically one or two substituents. Exemplary heteroaryl includes, but is not limited to, pyridyl, furanyl, thiophenyl, thiazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like. The terms "halo," "halogen" and "halide" are used interchangeably herein and refer to fluoro, chloro, bromo, or iodo. "Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, —$CH_2Cl$, —$CF_3$, —$CH_2CF_3$, —$CH_2CCl_3$, and the like.

When describing a chemical reaction, the terms "treating", "contacting" and "reacting" are used interchangeably herein, and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Typically, nitric acid having concentration of at least 10 N, often at least 15 N, and more often at least 24 N is used. While any anhydride can be used in the process of the invention, mainly for economic reasons, typically acetic anhydride is used in the process of the invention. However, it should be appreciated that the scope of the invention is not limited to any particular anhydride.

Generally, to control or avoid uncontrolled exothermic reaction between nitric acid and an anhydride, nitric acid is added slowly to the anhydride in the absence of any organic solvent. As used herein, the term "absence of any organic solvent" means that no inert (i.e., relatively non-reactive under the reaction condition) organic solvent is present in the reaction mixture (other than at most any trace amount of an organic solvent that may be present in the anhydride). In particular, the term "absence of any organic solvent" refers to having about 5% or less, typically about 1% or less, and often about 0.5% or less of organic solvent. The term "about" refers to ±20%, typically ±10%, and often ±5% of the numeric value.

Typically, the anhydride is at least about 95%, often at least about 98%, and more often at least about 99% pure. Nitric acid can be anhydrous nitric acid, fuming nitric acid, or an aqueous solution of nitric acid having the concentration disclosed herein. Typically, nitric acid is added to anhydride at temperature of about 20° C. or less, often at 10° C. or less, more often at 5° C. or less, and most often at or near 0° C. or below.

Without being bound by any theory, it is believed that addition of nitric acid to anhydride produces a highly reactive acylated nitrate intermediate compound, e.g., R—C(=O)—ONO$_2$. After addition of a desired amount of nitric acid to anhydride, the resulting solution is typically mixed (e.g., stirred) for a period of time, e.g., generally an hour or less, typically 30 minutes or less, and often 15 minutes or less. However, it should be appreciated that the reaction time between nitric acid and anhydride can vary depending on a variety of factors such as the concentration of nitric acid, the nature of anhydride, the amount of each reagents added, the reaction temperature, etc. Accordingly, the scope of the invention is not limited to any particular reaction time.

After adding nitric acid to anhydride, an aromatic compound is added to the reaction mixture to produce a nitrated aromatic compound. Again the reaction time and temperature can vary widely depending on a variety of factors discussed above. Typically, the resulting mixture is allowed to stir overnight. It should be appreciated that initially a mono-nitrated aromatic compound is formed. Upon further reaction, one can achieve dinitration of the aromatic compound. In some instances, the reaction temperature may be increased to facilitate formation of dinitration aromatic compound.

Nitrated aromatic compound can be readily separated from the reaction mixture by quenching the reaction mixture with water, and in many instances by precipitating out the nitrated aromatic compound or by extraction into an organic solvent.

The aromatic compound can be added to the reaction mixture in a concentrated form, i.e., neat, or it can be added as a solution using the anhydride as a solvent. In this manner, only the anhydride compound, which is already present, is typically used. It should be appreciated that it is also possible to add the aromatic compound as a solution in an inert organic solvent.

Other aspects of the invention provide a process for nitrating an optionally substituted phenyl compound. Such a process typically includes providing a reaction mixture consisting essentially of a mixture obtained by combining nitric acid and an anhydride compound; and adding an optionally substituted phenyl compound to the resulting mixture under conditions sufficient to produce a nitrated phenyl compound.

One particular aspect of the invention provides a process for producing 2,4-dinitroanisole using nitric acid and alkyl anhydride. The process involves producing a mixture that consists essentially of a mixture obtained from combining nitric acid and anhydride compound.

Yet other aspects of the invention provide processes for producing labeled nitroaromatic compounds, such as [$^{13}C_6$]-2,4-dinitroanisole (ring-$^{13}C_6$) from [$^{13}C_6$]-anisole (ring-$^{13}C_6$) and [$^{15}N_2$]-2,4-dinitroanisole from anisole using in situ generated activated [$^{15}N$]-nitrating reagent, respectively. Thus, treatment of [$^{13}C_6$]-anisole (ring-$^{13}C_6$) with the process of the invention gave [$^{13}C_6$]-2,4-dinitroanisole (ring-$^{13}C_6$) in a high yield. Treatment of anisole with activated [$^{15}N$]-nitrating reagent gave [$^{15}N_2$]-2,4-dinitroanisole in a good yield after two cycles of nitration. Byproducts in the latter reaction included [$^{15}N$]-2-nitroanisole and [$^{15}N$]-4-nitroanisole.

2,4-Dinitroanisole (DNAN, 1) is an insensitive munitions compound (IMC) in development to replace conventional energetic compounds (e.g., TNT) because of its improved resistance to heat and shock.[1] Although the technical properties of DNAN are well characterized, its environmental fate is poorly understood. DNAN and other nitroaromatic compounds can undergo extensive transformation in soil due to both microbial and abiotic processes. For example, nitro groups may be reduced in anaerobic soils,[2] leading to the formation of reactive aminoarene compounds that can undergo further transformations to oligomeric compounds[2] and/or to humus-bound residues.[3] Experiments with $^{13}C$ and $^{15}N$ stable isotope-labeled DNAN can help to reveal the products and (bio)transformation mechanisms of this energetic material through the use of $^{13}C$-NMR and $^{15}N$-NMR techniques[4] and by LC-MS/MS analysis for assignment of degradation product chemical structures. Microorganisms able to utilize carbon and/or nitrogen atoms from $^{13}C$- and $^{15}N$-labeled DNAN can be identified by a combination of DNA-stable isotope probing (SIP) and 16S-rRNA gene clone libraries[5] created from enrichment cultures with universal bacterial primers. The degradation rate and ultimate environmental fate of DNAN and intermediates, transformed into safe end products such as mineralized products and bound residue in humus, can be revealed by incubation experiments designed to determine the biotic and abiotic processes interacting on $^{13}C$- and $^{15}N$-labeled DNAN. Thus, to illustrate utility of the present invention, the process of the invention was used to produce $^{13}C$- and $^{15}N$-labeled compounds 2 and 3 in gram quantities.

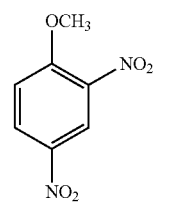

1

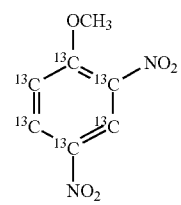

2

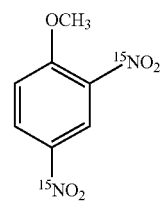

3

It should be noted that DNAN (1) has been previously prepared by mononitration of 2-nitroanisole or 4-nitroanisole,[6-8] or by dinitration of anisole in a single step.[9-12] The dinitration procedures were more appealing and included treatment of anisole with nitronium tetrafluoroborate,[9] urea nitrate-sulfuric acid,[10] urea nitrate-polyphosphoric acid,[11] and an acidic montmorillonite clay impregnated with anhydrous cupric nitrate (claycop).[12] However, as illustrated below in the Examples section, processes of the invention provided a more simple and efficient synthesis of DNAN from nitric acid and an anhydride.

Some aspects of the invention can be generalized by the following process or method. In this particular illustration, a process is provided for producing a nitro-substituted phenyl compound of Formula I:

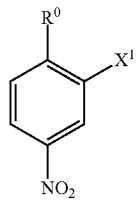

I

The process includes, contacting a concentrated nitric acid with an alkyl anhydride under conditions sufficient to produce a reactive intermediate; and adding a phenyl compound of the formula:

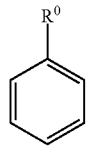

II to the reactive intermediate under conditions sufficient to produce a nitro-substituted phenyl compound of Formula I. In some embodiments, $R^0$ is H, alkyl, alkoxy, halide, alkylthiol (i.e., a moiety of the formula —SR, where R is alkyl), aryl, vinyl (or alkenyl), alkynyl, aminoacyl (e.g., a moiety of the formula —$NR^a$(=O)$R^b$, where $R^a$ is H or alkyl and $R^b$ is alkyl, aryl, aralkyl, cycloalkyl, (cycloalkyl)alkyl, etc.); and $X^1$ is H or $NO_2$. In some embodiments, $R^0$ is H, alkyl, alkoxy or halide. The term "alkylene" means a linear saturated divalent hydrocarbon moiety of one to twenty, typically one to twelve, and often one to six carbon atoms or a branched saturated divalent hydrocarbon moiety of three to twenty, typically three to twelve and often three to six carbon atoms, e.g., methylene, ethylene, propylene, 2-methylpropylene, pentylene, and the like. The term "alkenyl" means a linear monovalent hydrocarbon moiety of two to twenty, typically two to twelve, and often two to six carbon atoms or a branched monovalent hydrocarbon moiety of three to twenty, typically three to twelve and often three to six carbon atoms, containing at least one double bond, e.g., ethenyl, propenyl, and the like. The term "alkynyl" means a linear monovalent hydrocarbon moiety of two to twenty, typically two to twelve, and often two to six carbon atoms or a branched monovalent hydrocarbon moiety of three to twenty, typically three to twelve and often three to six carbon atoms, containing at least one carbon-carbon triple bond, e.g., ethynyl, propynyl, and the like.

Still in other embodiments, the process can further include the step of purifying the nitro-substituted phenyl compound of formula I. Any method or a combination of methods of purification known to one skilled in the art can be used including, but not limited to, chromatography (such as solid-liquid chromatography, HPLC, MPLC, etc.), recrystallization, distillation, filtration, etc. In one particular embodiment, the nitro-substituted phenyl compound of Formula I is purified by a recrystallization process.

Yet in one specific specific embodiment, $R^0$ is selected from the group consisting of H, methyl, ethyl, methoxy, ethoxy, chloro, and bromo.

The reaction temperature for adding nitric acid and the anhydride together can be any suitable temperature that does not cause any significant decomposition of the reactive intermediate for nitration step. Typically, the reaction temperature for generating the reactive intermediate is about 70° C. or less, often about 50° C. or less, more often about 30° C. or less, and most often about 10° C. or less. However, it should be appreciated that this reaction temperature can vary depending on a variety of factors including, but not limited to, the identity of the actual anhydride used, the amount of anhydride and/or the nitric acid used, etc.

The reaction temperature for adding an aromatic compound to the reactive intermediate can also be any suitable temperature that does not cause any significant decomposition of the reactive intermediate for nitration step. Typically, the reaction temperature for nitrating the aromatic compound with the reactive intermediate is about 70° C. or less, often about 50° C. or less, more often about 30° C. or less, and most often about 20° C. or less. However, it should be appreciated that this nitration reaction temperature can vary depending on a variety of factors including, but not limited to, the identity of the aromatic compound (e.g., presence or the absence of an electron donating or electron withdrawing substituent(s), the nature of the aromatic compound such as phenyl, thiophenyl, pyridyl, furyl, etc.) used, the amount of aromatic compound used, etc.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

All reagents and solvents were commercially available and were used as received. Solutions were concentrated in vacuo using a rotary evaporator. Analytical thin-layer chromatography (TLC) was performed on pre-coated silica gel 60 F-254 glass plates. TLC visualization required using UV light and/or staining. Anisaldehyde stain (100 mL anisaldehyde, 50 mL glacial AcOH, 100 mL conc $H_2SO_4$, 1 L 95% EtOH) and PMA stain (5 g phosphomolybdic acid, 100 mL 95% EtOH) were the most commonly used TLC stains. Flash and gravity chromatography were performed using silica gel 60 (230-400 mesh). Melting points are uncorrected. Nuclear Magnetic Resonance (NMR) experiments were performed on a 500 MHz spectrometer. NMR spectra were referenced to TMS (0.00 ppm) or $CDCl_3$ (7.26 ppm, 77.0 ppm). Mass spectrometry was conducted using GC/MS (EI, Shimadzu QP 2010 Ultra instrument) on a DB-5 column with a flow rate of 1 mL/min. High resolution mass spectrometry was conducted on an AB Sciex TripleTOF 5600 mass spectrometer using positive mode electrospray ionization.

Example 1

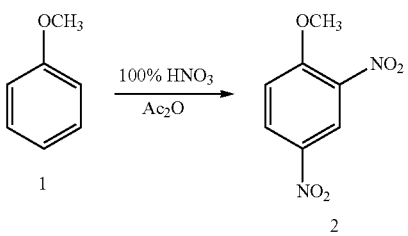 [SMILES: "Ac2O" ; COc1ccccc1 ; COc1ccc([N+](=O)[O-])cc1[N+](=O)[O-]]

Synthesis of DNAN (2):

Concentrated nitric acid (2.96 g, 47 mmol, 2 mL) was added dropwise to acetic anhydride (5 mL, 5.4 g, 53 mmol) at 0° C. with stirring. After 10 min, a solution of 1 (1.08 g, 10 mmol) in acetic anhydride (1 mL) was added dropwise and the mixture was allowed reach room temperature. After stirring overnight, the reaction mixture was poured into water (50 mL) and stirred for 1 hr. The crude solid was filtered and crystallized from 20% EtOAc/hexanes to afford 2 (1.62 g, 8.2 mmol) in 82% yield as colorless needles.

Synthesis of [$^{13}C_6$]-2,4-Dinitroanisole (2):

Concentrated nitric acid (2.96 g, 47 mmol, 2 mL) was added dropwise to acetic anhydride (5 mL, 5.4 g, 53 mmol) at 0° C. with stirring. After 10 min, a solution of 4 (1.14 g, 10 mmol, Sigma-Aldrich) in $CCl_4$ (3 mL) was added dropwise and the mixture was allowed reach room temperature. After stirring overnight, the reaction mixture was diluted with $CH_2Cl_2$ (200 mL) and washed with water (4×150 mL), brine (100 mL), and dried ($MgSO_4$). Volatiles were removed under reduced pressure and the residual oil loaded onto a flash silica gel column (100 g). Elution with 5% EtOAc/hexanes gave 5 (0.24 g, 1.50 mmol, 15%) as a light yellow solid. Further elution with 25% EtOAc/hexanes gave 2 (1.70 g, 8.33 mmol) as an off white crystalline solid in 83% yield. Recrystallization of 2 from 20% EtOAc/hexanes afforded colorless needles that melted at 86-87° C. $^1$H NMR (500 MHz, $CDCl_3$) d 4.10 (3H, d, J=4 Hz), 7.23 (1H, merged dd, J=167 Hz), 8.44 (1H, merged dd, J=172 Hz), 8.72 (1H, apparent d, J=173 Hz); $^{13}$C NMR (125 MHz, $CDCl_3$) d 57.4 (s), 113.6 (t, J=62 Hz), 121.8 (t, J=70 Hz), 129.1 (merged t, J=63 Hz), 138.7 (t, J=74 Hz), 140.0 (t, J=69 Hz), 157.2 (merged dt, J=72 Hz); GC/MS (EI, M$^-$) 204, $t_r$=12.4 min; HRMS (ESI$^+$) calculated m/z for (M+H)$^+$ 205.0551, observed 205.0586; calculated m/z for (M+Na)$^+$ 227.0370, observed 227.0372.

Synthesis of [$^{15}N_2$]-2,4-Dinitroanisole (3):

[$^{15}$N]-Nitric acid (10N, 4 mL, 40 mmol, Sigma-Aldrich) was added dropwise to acetic anhydride (21.64 g, 212 mmol, 20 mL) at 0° C. with stirring. After 10 min, a solution of anisole (6, 1.08 g, 10 mmol) in $CCl_4$ (3 mL) was added dropwise and the mixture was allowed to reach room temperature. After stirring for 24 h, the reaction mixture was diluted with $CH_2Cl_2$ (200 mL), washed with water (4×150 mL), brine (10 mL), and dried ($MgSO_4$). Volatiles were removed under reduced pressure and the residue subjected to a second nitration as just described. After the second workup, the residual oil was loaded onto a flash silica gel column (150 g). Elution with 5% EtOAc/hexanes gave 8 (0.19 g, 1.2 mmol, 12%) as a colorless solid. Further elution with 10% EtOAc/hexanes gave 7 (0.56 g, 3.6 mmol, 36%) as a yellow oil. Finally, elution with 25% EtOAc/hexanes gave 3 (0.88 g, 4.4 mmol, 44%) as an off-white crystalline solid. Recrystallization of 3 from 20% EtOAc/hexanes produced colorless crystals that melted at 86-87° C. $^1$H NMR (500 MHz, $CDCl_3$) d 4.10 (3H, s), 7.24 (1H, merged dd), 8.43-8.46 (1H, m), 8.72-8.75 (1H, m); $^{13}$C NMR (125 MHz, $CDCl_3$) d 57.4 (s), 113.6 (s), 121.8 (s), 129.1 (s), 138.8 (d, J=16 Hz), 140.1 (d, J=17 Hz), 157.2 (s); GC/MS (EI, M$^+$) 200, $t_r$=12.4 min; HRMS (ESI$^+$) calculated m/z for (M+H)$^+$ 201.0290, observed 201.0291; calculated m/z for (M+Na)$^+$ 223.0110, observed 223.0116.

Results and Discussion:

Prior to attempts at syntheses of 2 and 3, the claycop nitration of anisole was performed according to the published procedure,[12] which involved addition of a solution of anisole (10 mmol) in $CCl_4$ (30 mL) to a mixture of claycop (4.8 g, Sigma-Aldrich) and acetic anhydride (15 mL, 16 mmol). As described, ~6 equivalents of nitric acid were required to complete the nitration process. Acetic anhydride and nitric acid mixtures generate acetyl nitrate[13] in situ, and many examples of aromatic nitration with acetyl nitrate have been reported.[14,15] In order to check whether claycop was required for dinitration of anisole, dinitration was attempted with in situ generated acetyl nitrate. Thus, a solution of anisole (10 mmol) in $CCl_4$ was added dropwise to an ice-cold mixture of acetic anhydride (53 mmol) and 100% nitric acid (47 mmol). After stirring overnight at room temperature, the reaction mixture was diluted with $CH_2Cl_2$ and washed several times with water. The organic layer was dried, concentrated under reduced pressure, and the resulting oil subjected to flash silica gel column chromatography using 5% ethyl acetate/hexanes and 20% ethyl acetate/hexanes as elutants. DNAN (1) was obtained as a light yellow solid in 85% yield. $^{13}$C-labeled 2 was similarly prepared from [$^{13}C_6$]-anisole (ring-$^{13}C_6$, Sigma Aldrich) in 83% yield, along with [$^{13}C_6$]-4-nitroanisole (compound 5, 15% yield), as depicted in Scheme 1 below.

Scheme 1. Synthesis of [$^{13}C_6$]-2,4-dinitroanisole (2)

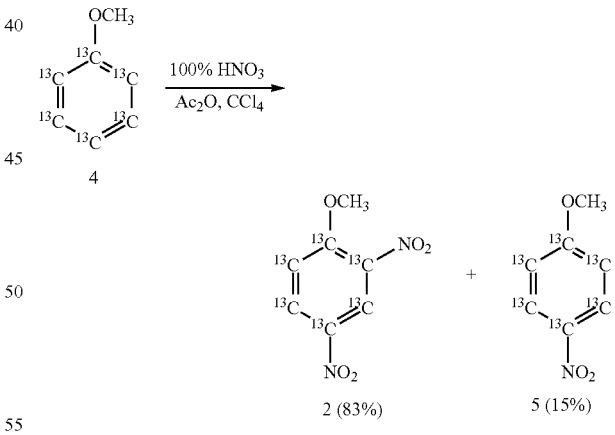

With $^{13}$C-labeled DNAN (2) in hand, $^{15}$N-labeled 3 was prepared from anisole. [$^{15}$N]-labeled nitric acid is available commercially as a 10 N solution in water. Therefore, synthesis of 1 from anisole using a 10N solution of nitric acid in water was conducted. To account for the presence of water, excess acetic anhydride was used. Thus, a solution of anisole (10 mmol) in $CCl_4$ was added dropwise to an ice-cold mixture of acetic anhydride (212 mmol) and 10N nitric acid (40 mmol). After 24 h of stirring at room temperature, TLC analysis of the reaction mixture indicated that 2-nitroanisole was the major product, with 1 and 4-nitroanisole as minor products. The reaction mixture was diluted with $CH_2Cl_2$ and washed several times with water. The organic layer was dried, concentrated under reduced pressure, and the residue subjected to a second treatment with acetic anhydride (212 mmol) and 10N nitric acid (40 mmol) as described above. TLC analysis indicated the presence of much more 1 after the second exposure to acetyl nitrate. After workup as described above, the resulting oil was subjected to flash silica gel column chromatography using 5% ethyl acetate/hexanes and 20% ethyl acetate/hexanes as elutants. DNAN (1) was obtained in 43% yield, along with 2-nitroanisole (7, 31% yield) and 4-nitroanisole (8, 12% yield). $^{15}$N-Labeled 3 was similarly prepared in 44% yield from anisole and [$^{15}$N]-acetyl nitrate generated in situ, along with [$^{15}$N]-2-nitroanisole (7, 36%) and [$^{15}$N]-4-nitroanisole (8, 12%) as depicted in Scheme 2 below.

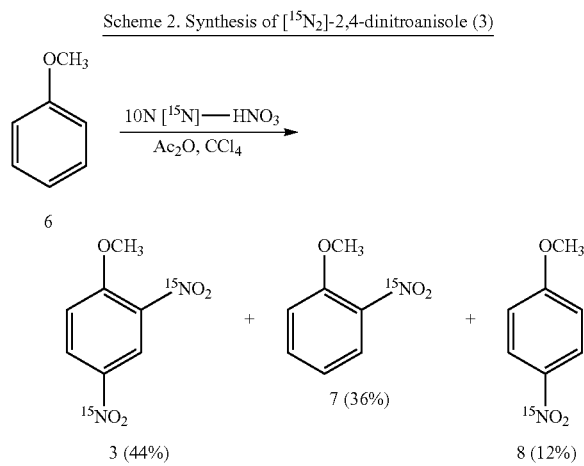

Conclusion:

The process of the invention can be used to prepare 2,4-dintroanisole (1) in good yield from anisole and acetyl nitrate generated in situ without the need for solid catalysts and/or solvents. Using this method, gram quantities of [$^{13}C_6$]-2,4-dinitroanisole (2) and [$^{15}N_2$]-2,4-dinitroanisole (3) have been prepared.

Example 2

In Example 1 above, a synthesis of 2,4-dinitroanisole from anisole and acetyl nitrate generated in situ is described using anhydride and concentrated (i.e., about 100% purity) nitric acid mixture without the need for solid catalysts. In this example, continued efforts to study the selectivity of nitration using in situ generated acetyl nitrate on various monosubstituted benzenes is described. In each case the experimental procedure reported in Example 1 for dinitration of anisole (10 mmol) was followed. Product mixtures were analyzed using $^1$H NMR spectral analysis. In some cases separation of product mixtures using gravity column chromatography on silica gel was also employed. Treatment of highly active phenetole with in situ generated acetyl nitrate gave a 9:1 mixture of 2,4-dinitrophenetole and 4-nitrophenetole in 90% combined yield. With the less reactive arenes ethylbenzene and toluene, however, more complex mixtures of mono- and dinitration products were obtained. Treatment of ethylbenzene with in situ generated acetyl nitrate followed by an aqueous workup gave an oil that was subjected to gravity column chromatography. Elution with 5% ethyl acetate/hexanes afforded an inseparable mixture of 1-ethyl-4-nitrobenzene and 1-ethyl-2-nitrobenzene (85% combined yield) in a 1.13:1 ratio. Further elution of the column with 10% ethyl acetate/hexanes gave an inseparable 5:1 mixture of 1-ethyl-2,4-dinitrobenzene and 1-ethyl-2,6-dinitrobenzene (11% combined yield). Toluene was similarly treated with in situ generated acetyl nitrate and the oil obtained after aqueous workup subjected to gravity column chromatography. Elution with 5% ethyl acetate/hexanes gave an inseparable 1.25:1 mixture of 4-nitrotoluene and 2-nitrotoluene (80% combined yield). Further elution of the column with 7% ethyl acetate/hexanes and 10% ethyl acetate/hexanes gave 2,6-dinitrotoluene (5% yield) and 2,4-dinitrotoluene (5% yield).

In contrast with more electron-rich arenes, halobenzenes gave predominantly mononitration products when treated with in situ generated acetyl nitrate. Chlorobenzene gave a 21:5:1 mixture of 1-chloro-4-nitrobenzene, 1-chloro-2-nitrobenzene, and 1-chloro-2,4-dinitrobenzene, respectively, in 76% combined yield. Bromobenzene gave a 7:1 mixture of 1-bromo-4-nitrobenzene and 1-bromo-2-nitrobenzene in 78% combined yield.

Procedure for Nitration of Phenetole Using Acetic Anhydride and Nitric Acid.

Concentrated nitric acid (3.0 g, 47 mmol, 2.0 mL) was added dropwise to acetic anhydride (5.0 mL, 5.4 g, 53 mmol) at 0° C. with stirring. After 10 min, a solution of phenetole (1.22 g, 10 mmol) in acetic anhydride (1.0 mL) was added dropwise and the mixture allowed to attain room temperature. After stirring overnight, the mixture was poured into water (50 mL) and stirred for 1 h. The solid was collected by filtration and dried to give 1.90 g of a 9:1 mixture of 2,4-dinitrophenetole and 4-nitrophenetole.

Procedure for Nitration of Ethylbenzene.

Concentrated nitric acid (3.0 g, 47 mmol, 2.0 mL) was added dropwise to acetic anhydride (5.0 mL, 5.4 g, 53 mmol) at 0° C. with stirring. After 10 min, a solution of ethylbenzene (1.06 g, 10 mmol) in acetic anhydride (1.0 mL) was added dropwise and the mixture allowed to reach room temperature. After stirring overnight, the mixture was diluted with $CH_2Cl_2$ (200 mL), washed with water (4×150 mL) and brine (10 mL), dried over anhydrous $MgSO_4$ and filtered. Volatiles were removed under reduced pressure and the residual oil loaded on a silica gel column. Elution with 5% ethyl acetate/hexanes gave an inseparable mixture of 1-ethyl-4-nitrobenzene and 1-ethyl-2-nitrobenzene (1.28 g, 85% combined yield). The product ratio was determined to be 1.13:1 by $^1$H NMR analysis. Further elution of the column with 10% ethyl acetate/hexanes gave a 5:1 mixture of 1-ethyl-2,4-dinitrobenzene and a 1-ethyl-2,6-dinitrobenzene (0.24 g, 11% combined yield).

Nitration of Toluene.

A similar procedure using toluene in place of ethylbenzene produced a 1.25:1 mixture of 4-nitrotoluene and 2-nitrotoluene (combined yield 80%), 2,6-dinitrotoluene (yield 5%), and 2,4-dinitrotoluene (yield 5%).

Procedure for Nitration of Chlorobenzene.

Concentrated nitric acid (3.0 g, 47 mmol, 2.0 mL) was added dropwise to acetic anhydride (5.0 mL, 5.4 g, 53 mmol) at 0° C. with stirring. After 10 min, a solution of chlorobenzene (1.12 g, 10 mmol) in acetic anhydride (1.0 mL) was added dropwise and the mixture allowed to attain room temperature. After stirring overnight the mixture was diluted with $CH_2Cl_2$ (200 mL), washed with water (4×150 mL) and brine (10 mL), dried over anhydrous $MgSO_4$, and filtered. Volatiles were removed under reduced pressure to afford a 21:5:1 mixture of 1-chloro-4-nitrobenzene, 1-chloro-2-nitrobenzene, and 1-chloro-2,4-dinitrobenzene (combined yield 76%).

Nitration of Bromobenzene.

A similar procedure using bromobenzene in place of chlorobenzene produced a 7:1 mixture of 1-bromo-4-nitrobenzene and 1-bromo-2-nitrobenzene (combined yield 78%).

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

REFERENCES

[1] P. Davies, A. Provatas, *Weapons Systems Division, Defence Science and Technology Organisation (DSTO)*, 2006.

[2] C. Olivares, J. Liang, L. Abrell, R. Sierra-Alvarez, J. A. Field, *Biotechnology and Bioengineering* 2013, 110, 6, 1595-1604.

[3] K. Thorn, K. Kennedy, *Environmental Science & Technology* 2002, 36, 3787-3796.

[4] P. G. Hatcher, J. M. Bortlatynskl, R. D. Minard, J. Dec, J-M. Bollagg, *Environ. Sci. Technol.* 1993, 1003, 27, 2098-2103.

[5] J. D. Neufeld, J. Vohra, M. G. Dumont, T. Lueders, M. Manefield, M. W. Friedrich, J. C. Murrell, *Nat. Protocols* 2007, 2, 860-866.

[6] G. Aridoss, K. K. Laali, *J. Org. Chem.* 2011, 76, 8088-8094.

[7] J. Jacoway, G. G. K. S. Narayana Kumar, K. K. Laali, *Tetrahedron Lett.* 2012, 53, 6782-6785.

[8] R. Iqbal, N. H. Rama, M. Z. U. Haq, F. A. Madhwa, *J. Chem. Soc. Pak.* 1997, 19, 141-144.

[9] R. Iriye, T. Mukai, *Agr. Biol. Chem.* 1976, 40, 219-220.

[10] M. P. Majumdar, N. A. Kudav, *Indian J. Chem. Sec B* 1976, 14B, 1012-1013.

[11] V. B. Nabar, N. A. Kudav, *Indian J. Chem. Sec B* 1977, 15, 89-90.

[12] B. Gigante, Â. O. Prazeres, M. J. Marcelo-Curto, A. Cornélis, P. Laszlo, *J. Org. Chem.* 1995, 60, 3445-3447.

[13] R. Andreozzi, R. Marotta, R. Sanchirico, *J. Hazard. Mater.* 2002, 90, 111-121.

[14] K. Schofield, Aromatic Nitration, Cambridge University Press, Cambridge, UK 1980, pp. 54-71.

[15] M. C. Davis, T. J. Groshens, *Tetrahedron Lett.* 2012, 53, 4154-4155.

[16] K. Smith, M. H. Alotaibi, G. A. El-Hiti, *J. Catal.* 2013, 297, 244-247.

What is claimed is:

1. A process of producing 2,4-dinitroanisole in the absence of any catalyst, said process consisting of:
   contacting a concentrated nitric acid with an alkyl anhydride under conditions sufficient to produce a reactive intermediate; and
   adding anisole to the reactive intermediate in the absence of any catalyst under conditions sufficient to produce 2,4-dinitroanisole at a yield of at least 50%.

2. The process of claim 1 further comprising the step of purifying the dinitroanisole.

3. The process of claim 1, wherein said alkyl anhydride is of the formula:

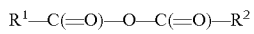

wherein each of $R^1$ and $R^2$ is independently hydrogen, alkyl, haloalkyl, cycloalkyl, (cycloalkyl)alkyl, aryl or aralkyl, or $R^1$ and $R^2$ together with the anhydride moiety form a ring structure.

4. The process of claim 3, wherein each of $R^1$ and $R^2$ is independently $C_1$-$C_6$ alkyl.

5. The process of claim 3, wherein each of $R^1$ and $R^2$ is independently methyl, ethyl, propyl, t-butyl, iso-butyl, butyl, iso-propyl, trifluoromethyl, or benzyl, or said alkyl anhydride compound is succinic anhydride.

6. The process of claim 1, wherein said alkyl anhydride is acetic anhydride.

* * * * *